United States Patent [19]
Johnson et al.

[11] Patent Number: 4,806,316
[45] Date of Patent: Feb. 21, 1989

[54] DISPOSABLE DEVICE FOR USE IN CHEMICAL, IMMUNOCHEMICAL AND MICROORGANISM ANALYSIS

[75] Inventors: Raymond Johnson, Mount Longstanton, England; Dwight Livingston; Robert C. Tite, both of Baltimore, Md.; Sheila J. Wood-Helie, Hampstead, Md.

[73] Assignee: Becton, Dickinson and Company, Franklin Lakes, N.J.

[21] Appl. No.: 27,280

[22] Filed: Mar. 17, 1987

[51] Int. Cl.$^4$ .................... G01N 1/28; G01N 21/00; G01N 31/22

[52] U.S. Cl. .................... 422/100; 422/58; 422/61; 436/164; 436/165; 435/33; 435/40; 435/293; 435/301; 435/810

[58] Field of Search .......... 422/58, 61, 100; 436/164, 165; 435/33, 34, 40, 287, 291, 293, 299, 300, 301, 810

[56] References Cited

U.S. PATENT DOCUMENTS

| | | | |
|---|---|---|---|
| 3,957,583 | 5/1976 | Gibson et al. | 435/33 |
| 4,018,652 | 4/1977 | Lanham et al. | 422/58 X |
| 4,116,775 | 9/1978 | Charles et al. | 435/34 |
| 4,207,394 | 6/1980 | Aldridge, Jr. et al. | 422/61 X |
| 4,318,994 | 3/1982 | Meyer et al. | 435/808 X |

Primary Examiner—Barry S. Richman
Assistant Examiner—Lynn Kummert
Attorney, Agent, or Firm—Mary M. Allen

[57] ABSTRACT

A substantially rigid, multi-well, self-pipetting device for use in chemical, immunochemical and microorganism analysis is provided. It includes a frame and a plurality of test wells disposed within the frame. A filing manifold communicates with each of the test wells through a filling passageway. A docking port on the periphery of the device receives a reservoir holding a fluid specimen. The docking port communicates with the filling manifold through a filling port and a filling channel. A vent control system also communicates with the test wells and is comprised of one or more vent manifolds, and/or valves to a vent manifold, and/or one or more vent holes to the ambient atmosphere. Any vent holes present are temporarily closed. With the device in its operational position, the test wells, filling channel, filling manifold and filling port are located at a level lower than the surface of the fluid in the reservoir, and the vent manifold and/or vent holes are positioned higher than the surface of the fluid in the reservoir. The test wells are connected to the filling manifold and the vent control system according to the filling sequence. The reservoir is also connected to the vent control system through a vent port and a vent channel. In use, the fluid specimen in the reservoir flows to the filling manifold and fills the test wells vented to the reservoir or to the ambient atmosphere.

23 Claims, 6 Drawing Sheets

DISPOSABLE DEVICE FOR USE IN CHEMICAL, IMMUNOCHEMICAL AND MICROORGANISM ANALYSIS

FIELD OF THE INVENTION

The present invention relates to a device for use in exposing a sample to be tested to one or more test reactants, and more particularly, the present invention relates to an apparatus and process which may be adapted to micoorganism identification, enzymatic analysis, chemical detection of components in the sample, immunological detection of antigen/antibody, quantitative analysis of reactants, including antigen/antibody immunological reactions and immobilized antigen assays.

BACKGROUND OF THE INVENTION

The present invention relates to a process and apparatus for analyzing fluid specimens for the presence of a substance or for a quantitative part of a substance contained in the specimen and more particularly to a process and apparatus for detecting, analyzing, and identifying microorganisms.

The conventional procedure for detecting and identifying microorganisms involves collecting a specimen and inoculating a part of this specimen onto a solid media which supports the growth of microorganisms. After incubation, the culture is examined for growth. Pure colonies are transferred to a series of test media for identification. Mixed cultures may require an additional isolation step if pure colonies are not available. The conventional time frame for the confirmatory identification of microorganisms from patient specimens ranges from 48 to 72 hours.

Other types of chemical analysis rely on the introduction of a sample to one or more test wells containing different reactive materials followed by observation of the reaction of the liquid specimen with the materials.

The present invention is directed toward providing a disposable, easily used device wherein a liquid specimen or prepared broth containing a microorganism can be introduced into one or more test wells with a minimum of manipulative steps. At a designated time, the liquid specimen in a particular well can be moved to one or more additional wells for one or more additional detection steps.

PRIOR ART

U.S. Pat. No. 4,207,394 to Aldridge Jr. et al is directed to a cartridge device for use in the analysis of specimens for the presence of microorganisms therein. The analysis device of the Aldridge et al Patent, however, is complex and is not completely self-contained. The apparatus of the Aldridge et al Patent includes a cassette which contains a serpentine flow channel having a series of filters therein and a detection cell located downstream from each filter. The flow channel in each cassette contains a culture medium which is freeze-dried and is highly selective in the sense that it promotes the growth of one type of microorganism but not others. A mixture of the specimen and water flows from a manifold into the flow channel of each cassette where it rehydrates the culture medium therein and further flows through the filters. Each filter removes a known proportion of the microorganisms from the mixture of specimen, water and medium, thereby effecting a serial dilution. After incubation, a detection cell is used to observe growth of any microorganisms therein which is manifested by a change in the light transmitting characteristics of the mixtures within the cells.

Other microtiter apparatus and disposable inoculation devices and cartridges are described in U.S. Pat. No. 4,154,795 to Thorne, U.S. Pat. No. 4,090,920 to Studer Jr., U.S. Pat. No. 4,318,994 to Meyea et al, U.S. Pat. No. 4,018,652 to Lanham et al and U.S. Pat. No. 4,028,151 to Fadler et al. The prior art devices disclosed in the foregoing referenced patents differ substantially from the disposable, gravity fill, self-pipetting cartridge of the present invention in ease of use and elimination of accessory tools and filling equipment.

SUMMARY OF INVENTION

An object of the present invention is to provide an improved apparatus and process for introducing a specimen into one or more test wells.

Another object of the present invention is to provide a device that is self-filling by means of gravity.

Another object of the present invention is to provide a self-filling device that is disposable, self-contained, and low cost.

Another object of the present invention is to provide a simple apparatus and method for rehydrating one or more test wells with an aliquot of liquid specimen by gravity fill.

Another object of the present invention is to provide a self-filling device having multiple test wells which are isolated from each other in such manner as to prevent cross contamination.

Another object of the present invention is to provide a self-filling device having multiple test wells which are isolated from each other but which can be interconnected in a desired configuration for performance of a series of tests by moving a sample from one test well to another.

Another object of the present invention is to allow entrance into a specified well or specified set of wells by a fluid specimen at a designated time.

Another object of the present invention is to allow movement of a reaction mixture in a well or set of wells to an additional area or areas following predesignated incubation period(s).

Another object of the present invention is to provide a device which allows analysis to proceed rapidly, with no contamination of the environment, and no need for any additional accessories to perform the analysis.

Generally, in accordance with the most simple embodiment of the present invention, a substantially rigid, multi-well, self-pipetting device for use in chemical, immunochemical and microorganism analysis is provided. The device includes a substantially rigid, substantially planar frame having, in operational orientation, a front face, a back face, a top edge and a bottom edge. A plurality of test wells are disposed within the device between the front face and the back face, usually in a linear array. A filling manifold is located within the device. The filling manifold is in fluid communication with each of the test wells through a filling passageway. A docking port is provided in the device which is adapted for receiving a reservoir holding a fluid specimen. The docking port is disposed on a peripheral surface of the device. The docking port is in fluid communication with the filling manifold through a filling port and filling channel disposed within the device. With the device in its operational orientation, the test wells, filling channel, filling manifold and filling port are located at a level lower than the surface of the fluid in the reservoir.

The device has a vent control system, also in fluid communication with the test wells, which is comprised of one or more vent manifolds, and/or valves to a vent manifold, and/or one or more vent holes or other passages to the ambient atmosphere. These vent holes, if present, are temporarily closed by a film or other means. With the device in its operational position, the vent manifold and/or vent holes of the vent control system are positioned higher than the surface of the fluid in the reservoir. The test wells are connected to parts of the filling manifold and the vent control system according to the filling sequence. The reservoir is also connected to the vent control system through a vent port and a vent channel. The fluid specimen in the reservoir therefore flows down to the filling manifold by gravity and fills the test wells vented to the reservoir or to the ambient atmosphere.

Other test wells are sometimes subsequently filled by venting them to the reservoir, to outside air or to another test well at a higher level. The other test well may be filled by fluid from another test well, or from the filling manifold.

The test wells contain appropriate reagents that may interact to cause a visible or otherwise detectable change in the sample, or prepare the sample for subsequent wells, or prepare a solution to be used for the test. Visible results may be seen through a clear window in the well. Wells may have a clear window to view results, two clear faces for photo analysis, or otherwise configured according to appropriate analysis. Reagents in the wells are dry, viscous, or contained from flowing through the device by a blotter, seal, or other means that allows mixing with the sample.

BRIEF DESCRIPTION OF THE DRAWINGS

Other and further objects, advantages and features of the invention will be apparent to those skilled in the art from the following detailed description thereof, taken in conjunction with the accompanying drawings; wherein.

DETAILED DESCRIPTION OF THE INVENTION

Figure 1:
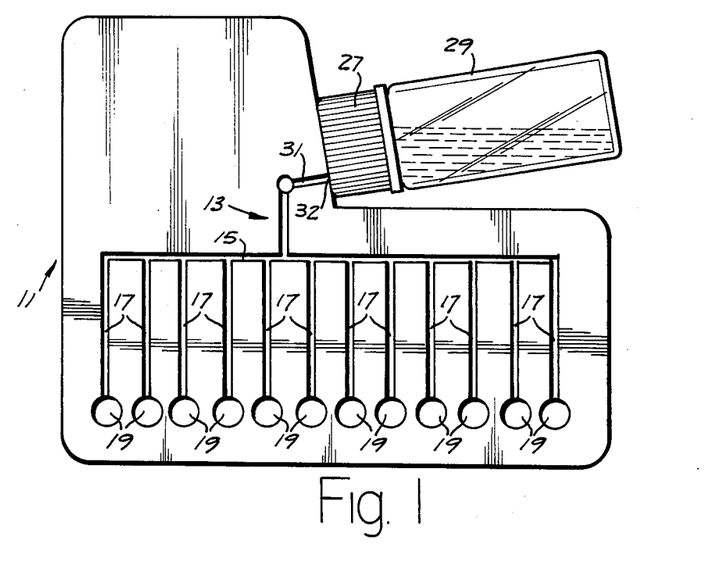
FIG. 1 is a front plan view of a disposable, self-contained multi test well device in accordance with one embodiment of the present invention showing the intake manifold arrangement.
Figure 2:
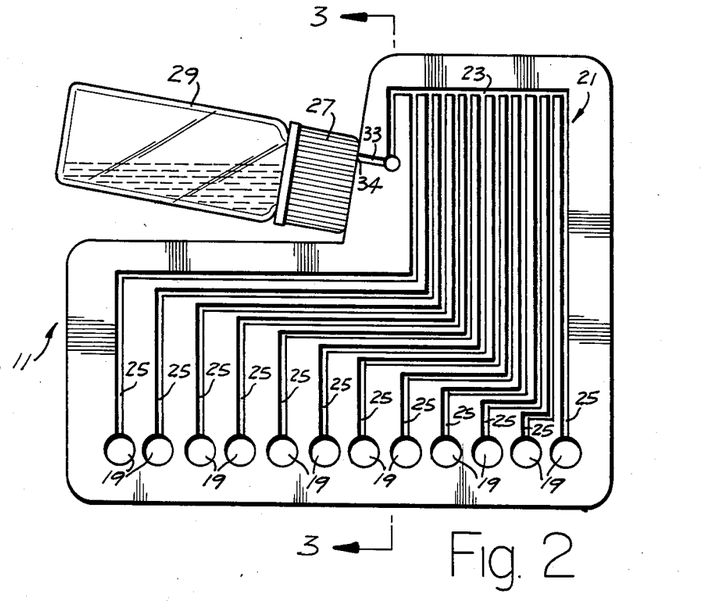
FIG. 2 is a back plan view of the device of FIG. 1 showing the vent manifold arrangement.
Figure 3:
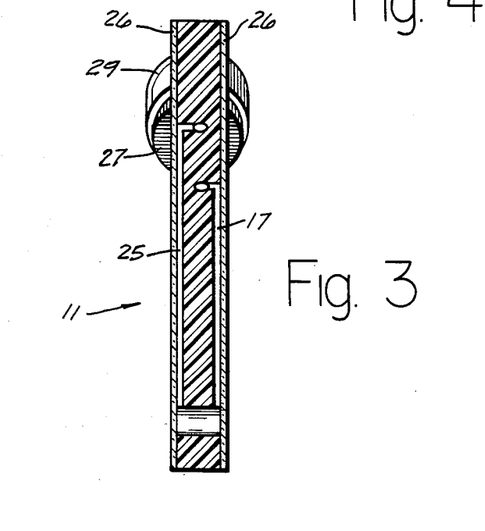
FIG. 3 is an end view of the disposable device shown in FIGS. 1 and FIG. 2.

As shown in FIGS. 1, 2 and 3, the disposable, multi-well, self-pipetting device of the present invention consists of a frame 11 made from a solid block of acrylic plastic or other suitable material. As shown in FIG. 1 a filling manifold system 13 is formed in the surface of the frame by machining of grooves or other suitable method. The filling manifold system 13 includes a filling manifold 15 and a series of filling passageways 17 leading from the filling manifold 15 to each of a series of test wells 19. As shown in FIG. 2 a venting manifold system 21 is formed in a similar fashion on the back side of the frame 11. The venting manifold system 21 includes a venting manifold 23 and a series of venting passageways 25 leading from the test wells 19 to the venting manifold 23. The filling manifold system 13 and the venting manifold system 21 are machined or otherwise formed on opposite sides of the frame 11. The test wells 19 are drilled or otherwise formed through the frame. After the frame has been formed with the filling manifold system 13 on one side and the venting manifold system 21 on the other side and the test wells 19 have been drilled therein, the cartridge is completed by gluing or otherwise securing a flexible or rigid sheet 26 of transparent plastic or other suitable material onto the front side and back side of the frame.

A docking port 27 is formed on a peripheral surface, which can be an edge or planar surface, of the frame 11. The docking port 27 is adapted to receive a specimen reservoir or vial 29. As shown in FIGS. 1 and 2 the docking port 27 comprises a screw type cap which is affixed to the periphery of the frame 11. The screw cap receives the threads of a specimen vial 29 when it is desired to use the cartridge of the invention. A filling channel 31 is drilled or otherwise formed through the frame 11 and leads from a filling port 32 to form a fluid communication channel with the filling manifold system 13. A venting channel 33 is also drilled or otherwise formed through the frame 11 and leads from a venting port 34 to form a fluid communication channel with the venting manifold system 21.

In use, a reservoir 29, such as a vial, containing a sample of inoculated serum or other fluid specimen is screwed into a mating relationship with the docking port 27. The device is oriented in a vertical position and is placed in a rack for incubation of the inoculum. As a kit, the test wells 19 are provided with a variety of dry chemicals such as freeze-dried carbohydrate media, prior to sealing the test wells, which react with various microorganisms or other analytes of interest. A color change in a series of test wells indicates the reactants which react with the microorganism to provide identification of the microorganism.

Figure 9:
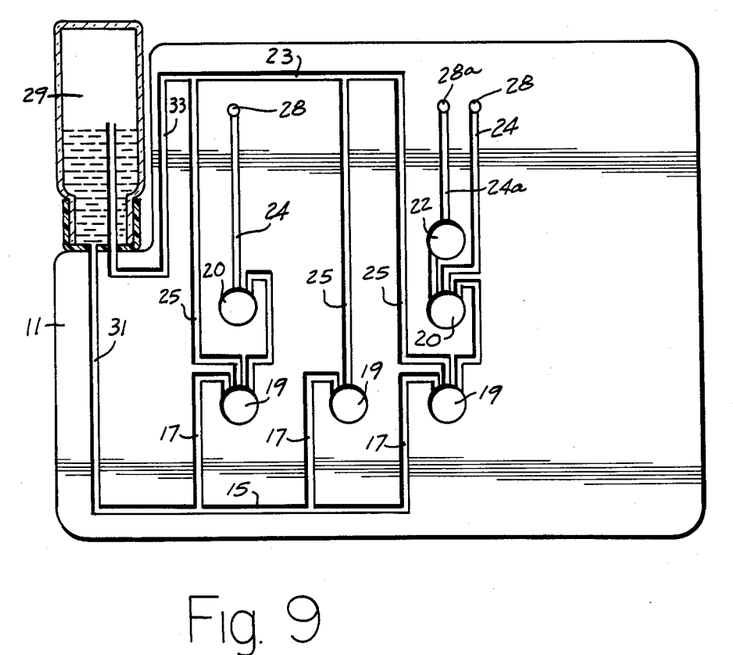
FIG. 9 is front plan view of a further embodiment of the disposable device of the present invention illustrating various arrays of wells suitable for sequential manipulation of a sample.

Gravity is used to move the fluid specimen with no need for a pressure or vacuum source. The junction of the venting passageways 25 with the venting manifold 23 of the venting system 21 is always at an elevation higher than the surface of the fluid in the reservoir 29 when the device is located in its operational position. Usually the entire venting manifold is at an elevation higher than the surface of the fluid, although sections of the venting manifold 23 between the junction of the venting passageways 25 and the venting manifold could be lower than the surface of the fluid. As shown in FIGS. 1, 2, 3, 4 and 5 the venting port 34 of the venting manifold system 21 is also positioned higher than the surface level of the liquid specimen in the vial when the device is inverted into operating position. For other embodiments of the device where the venting port 34 would be lower than the surface level of the liquid specimen, such as shown in FIGS. 5 and 9, a vent extension tube may be provided to move the venting port 34 above the liquid level, although this is optional, since air which is displaced by advance of fluid into the test wells would bubble thrpugh the fluid in the reservoir. Air in the system vents through the venting manifold 23, and through venting channel 33 into the serum vial.

The intake manifold 15 can be positioned at any point lower than the filling port 32. The positioning of the vent manifold 23 above the surface of fluid in the reservoir assures that all of the test wells will fill and not be cut off by fluid from another test well. The venting manifold 23 of the venting manifold system 21 is positioned higher than the surface level of the fluid in the reservoir when the device is located in its operating position. Such positioning of the venting manifold 23 assures that all of the test wells will fill and not be cutoff by fluid from another test well. Flow of the fluid is from the reservoir into the filling manifold system 13, into the test wells 19, out of the test wells 19 and into the venting manifold system 21 and out of the venting manifold system 21 through venting channel 33 and back into the serum vial.

The disposable, self-pipetting, multi-well device of the present invention provides a disposable cartridge for the delivery of small amounts (about 100 microliters) of fluid to a series of wells from one source. Gravity is used to move the fluid without need for the provision of a pressure source or a vacuum source. As shown in FIG. 1, when located in operational position, the venting port 34 of the venting manifold system 21 at the end of the venting channel 33 is higher than the inlet at the end of the filling channel 31 which connects with the filling manifold system 13.

Figure 4:
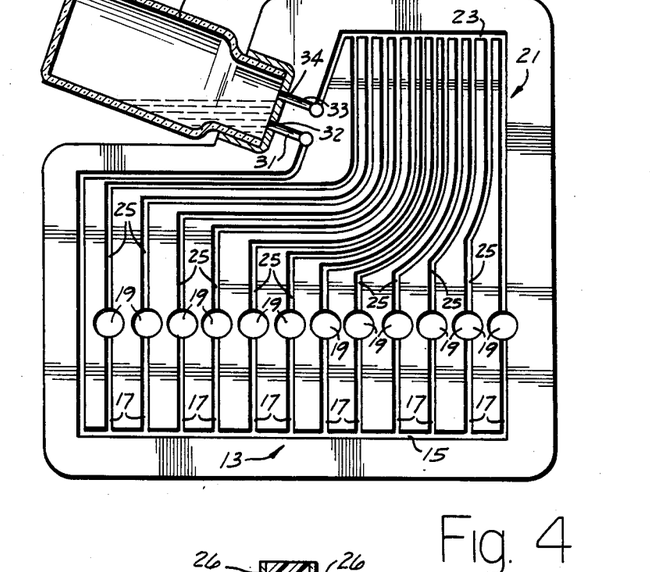
FIG. 4 is a front plan view of a further embodiment of the disposable device of the present invention.
Figure 5:
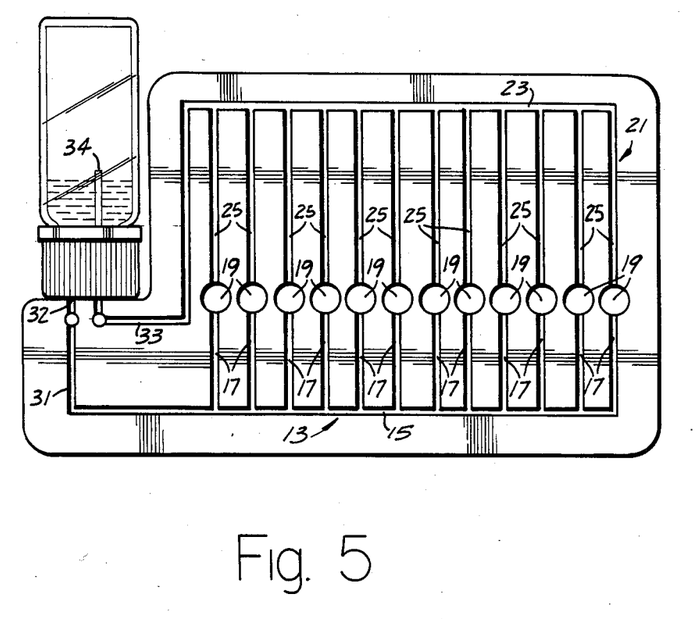
FIG. 5 is a front plan view of a still further embodiment of the disposable device of the present invention.
Figure 6:
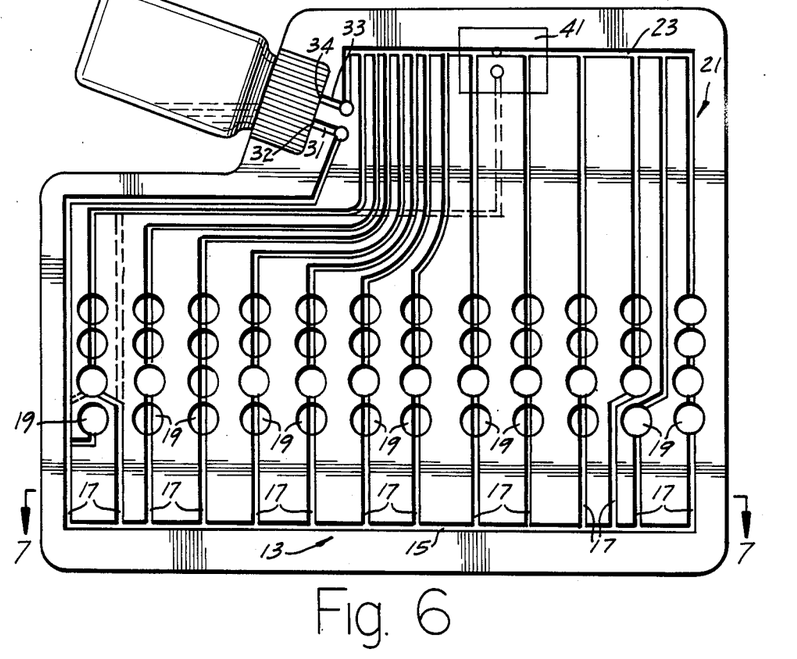
FIG. 6 is a front plan view of further embodiment of the disposable device of the invention showing a sequential array of test wells wherein the sample can be moved from a first test well to a sequence of test wells.

As shown in FIGS. 4, 5 and 6, which are further embodiments of the disposable device of the invention, the intake manifold and the venting manifold may be located on the same side of the frame 11. In each of these embodiments, the intake manifold 15 is located below the test wells and the filling port. As shown in FIGS. 4, 5 and 6, the configuration of the disposable, multi-well, self-pipetting device of the present invention is adapted to many variations without departing from the scope of the invention. It should be understood that other variations are also included within the scope of the invention. For example, while the devices shown in drawings are depicted with planar frames, the frame could be made curvilinear or cylindrical. Also, the frame could be folded on either a vertical or horizontal axis. Curving or folding the frame would provide a device which would be capable of self alignment into a standup operational position.

Figure 7:
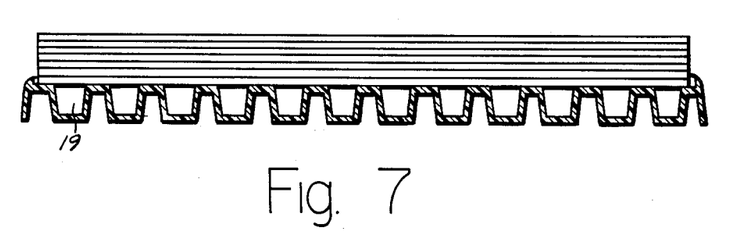
FIG. 7 is a side view of FIG. 8.
Figure 8:
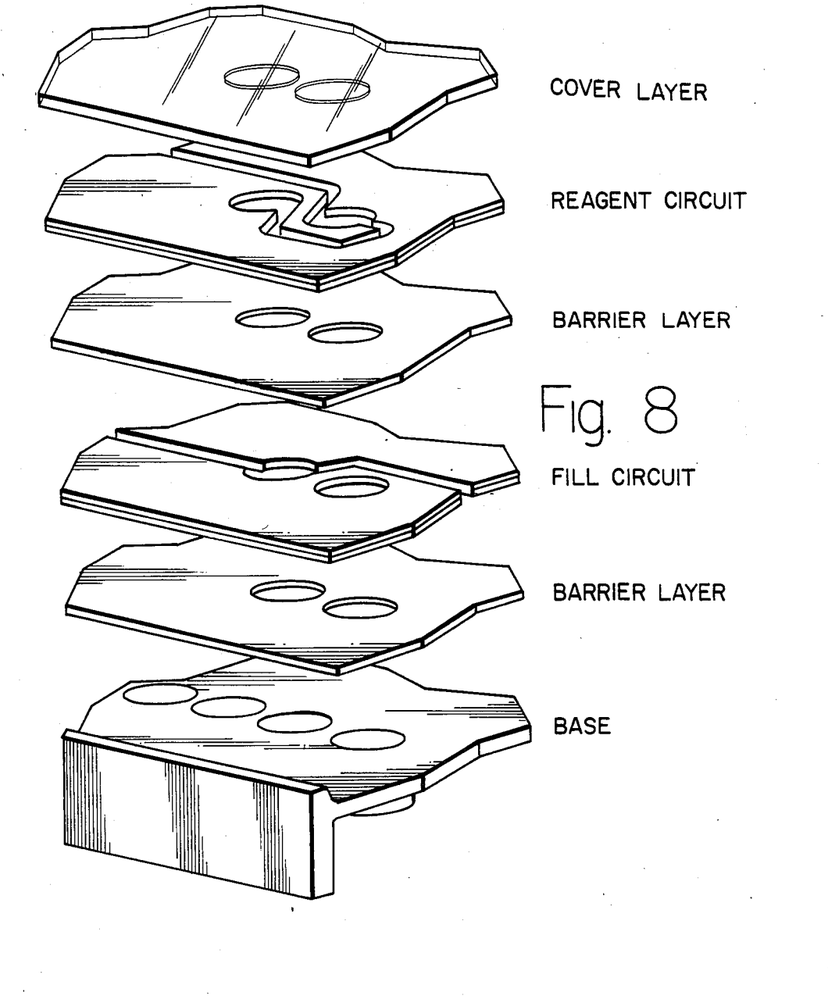
FIG. 8 is an exploded, partially broken away view showing the laminar construction of FIG. 7.

As shown in FIGS. 6, 7 and 8, the frame of the disposable device of the present invention can be made by lamination of several layers. As shown in FIG. 6, a reagent reservoir 41 is provided within the frame for dispensing a secondary reagent to preselected test wells for observation of the reaction of the reagent with the specimen. A reservoir within the frame could also be the primary reservoir obviating this need for docking port 27 and reservoir 29. The routing circuit for distribution of the specimen through the intake, manifold system 13 and the venting manifold system 21 with routing of the reagent in the reagent reservoir 41 is shown in FIG. 6. Any desired circuit of movement of the specimen through a series of test wells can be provided by altering the laminar construction shown in FIG. 8.

Laminations can be added to allow for utilization of specified wells. Selected wells can remain visible and selected wells can be filled. Time regulated fluid reaction may be implemented using one of several arrangements; three possibilities include ladder channel arrangement, liposome technology, or the use of dissolvable crystals. Originally filled wells can be allowed to move to adjacent wells by venting through pierced vent hole or by valve placement. Vent holes may be resealed using removable tape or other suitable material. The laminar layers shown in FIG. 7 may be made with sheet material or may be molded to result in fewer layers with the same result.

As shown in FIG. 9, the diversity of manipulation of the multi-well, self-pipetting device of the invention is illustrated. The device in FIG. 9 is prepared by machining or otherwise forming the filling manifold 15, the filling passageways 17, the filling channel 31, the venting manifold 23, the venting passageways 25, the venting channel 33 and primary test wells 19 in a suitable frame 11. In addition, secondary test wells 20 and a tertiary test well 22 are formed in the frame 11. Auxiliary venting passageways 24 lead from test wells 20 to a terminus vent hole 28 near the top of the frame. A venting passageway 24a leads from test well 22 to a terminus vent hole 28a. When the device is completed by securing a flexible sheet (not shown) to the face of the frame 11, the vent holes 28 and 28a of the venting passageways 24 to and 24a respectively are closed.

In use, the fluid specimen in the vial 29 first fills test wells 19 which are in return communication with the vial through the venting manifold system 21. Test wells 20 and 22 will not fill because of back pressure produced by blocking of auxiliary venting passageways 24 and 24a at the vent holes 28 and 28a. When the flexible sheet 26 is pierced at the vent hole 28 with a suitable object, such as the tip of pencil, the venting passageways 24 become open to ambient pressure and the fluid specimen will proceed from test wells 19 to test wells 20. When the flexible sheet 26 is pierced at the vent hole 28a, the venting passageway 24a becomes open to ambient pressure and the fluid specimen will proceed from test well 20 to test well 22. Of course, many combinations of one, two, three or more test well configurations can be devised for a single testing device depending on the chemical reactions or manipulations required for the fluid specimen.

What is claimed is:

1. A multi-well, self-pipetting device for use in chemical, immunochemical and microorganism analysis, said device comprising:
   (1) a frame having in operational orientation a body and a periphery;
   (2) a plurality of test wells disposed within said body;
   (3) a filling manifold located within said frame, said filling manifold being in fluid communication with each of said plurality of test wells;
   (4) a venting manifold located within said frame in a position above the filling manifold and above the plurality of test wells, said venting manifold being in fluid communication with each of said plurality of test wells; and
   (5) a docking port for receiving a container holding a fluid specimen, said docking port being located on the periphery of said frame, said docking port being in fluid communication with said filling manifold and with said venting manifold.

2. A device in accordance with claim 1 wherein said docking port is located in an intermediate position between said filling manifold and said venting manifold.

3. A device in accordance with claim 1 wherein a reservoir for containing a fluid specimen is affixed to said docking port.

4. A kit including the device of claim 1 having reagents disposed in said plurality of test wells.

5. A device in accordance with claim 1 comprising at least a base layer, a passageway circuit layer and a cover layer laminated together.

6. A device in accordance with claim 1 wherein a reservoir for containing a fluid reagent is disposed within said frame.

7. A device in accordance with claim 1 which is formed in a curvilinear shape.

8. A device in accordance with claim 1 wherein predetermined groups of the plurality of test wells are coupled in sequence by interconnecting passageways.

9. A device in accordance with claim 8 wherein an auxiliary venting passageway is in fluid communication with at least one of said plurality of test wells of one of said groups, said auxiliary passageway being isolated from said venting manifold and said auxiliary passageway leading to a venting port and means for exposing said venting port to ambient pressure or to fluid communication with said venting manifold.

10. A device in accordance with claim 1 comprising a base and a second piece laminated together.

11. A device in accordance with claim 10 further comprising a third piece laminated together with the base and the second piece, and the base is substantially planar having a first surface and a second surface, and has said plurality of test wells bored therethrough; said manifolds and passageways are formed on the first surface of the base; the second piece is a mating cover which is secured to the first surface of said base; and the third piece is a mating cover which is secured to the second surface of said base.

12. A device in accordance with claim 10 wherein the base is substantially planar; said plurality of test wells, manifolds and passageways are formed on a surface of the base; and the second piece is a mating cover which is secured to the surface of said base.

13. A device in accordance with claim 12 having an axis in the substantially planar base about which the device is folded.

14. A multi-well, self pipetting device for use in chemical, immunochemical and microorganism analysis, said device comprising:

(1) a frame having in operational orientation a body and a periphery;
(2) a plurality of test wells disposed within said body;
(3) a filling manifold located within said frame, said filling manifold being in fluid communication with each of said plurality of test wells;
(4) a venting manifold located within said frame in a position above the filling manifold and above the plurality of test wells, said venting manifold being in fluid communication with each of said plurality of test wells; and
(5) a reservoir for containing a fluid reagent disposed within said frame, said reservoir being in fluid communication with said filling manifold and said venting manifold.

15. A kit including the device of claim 14 having reagents disposed in said plurality of test wells.

16. A device in accordance with claim 14 comprising at least a base layer, a passageway circuit layer and a cover layer laminated together.

17. A device in accordance with claim 14 which is formed in a curvilinear shape.

18. A device in accordance with claim 14 wherein predetermined groups of the plurality of test wells are coupled in sequence by interconnecting passageways.

19. A device in accordance with claim 18 wherein an auxiliary venting passageway is in fluid communication with at least one of said plurality of test wells of one of said groups, said auxiliary passageway being isolated from said venting manifold and said auxiliary passageway leading to a venting port and means for exposing said venting port to ambient pressure or to fluid communication with said venting manifold.

20. A device in accordance with claim 14 comprising a base and a second piece laminated together.

21. A device in accordance with claim 20 further comprising a third piece laminated together with the base and the second piece, and the base is substantially planar having a first surface and a second surface, and having said plurality of test wells bored therethrough; said manifolds and passageways are formed on the first surface of the base; the second piece is a mating cover which is secured to the first surface of said base; and the third piece is a mating cover which is secured to the second surface of said base.

22. A device in accordance with claim 20 wherein the base is substantially planar having said plurality of test wells, manifolds and passageways formed on a surface thereof and the second piece is a mating cover which is secured to the surface of said base.

23. A device in accordance with claim 22 having an axis in the substantially planar base about which the device is folded.

* * * * *